United States Patent [19]

Uddo Jr. et al.

[11] Patent Number: 4,878,762
[45] Date of Patent: Nov. 7, 1989

[54] SECRETION CONTAMINATED INDWELLING TUBE CLOSED REMOVAL AND DISPOSAL SYSTEM

[76] Inventors: Joseph F. Uddo Jr., 1201 Ridgelake Dr., Metairie, La. 70001; John R. Breaux, 327 Bonnebel Blvd., Metairie, La. 70005

[21] Appl. No.: 143,177

[22] Filed: Jan. 13, 1988

[51] Int. Cl.⁴ .............................................. B65B 39/06
[52] U.S. Cl. ..................................... 383/33; 141/316; 141/390; 206/365; 248/99; 604/171
[58] Field of Search ......................... 604/163, 171–172; 383/33; 248/99; 141/316, 390, 391; 128/DIG. 24; 206/364, 365, 366

[56] References Cited

U.S. PATENT DOCUMENTS

| | | | |
|---|---|---|---|
| 755,085 | 3/1904 | Viano | 248/99 |
| 1,120,549 | 12/1914 | Schellberg | 604/171 |
| 2,430,155 | 11/1947 | Buttery | 141/390 |
| 3,154,080 | 10/1964 | Rowan et al. | 604/171 |
| 3,843,041 | 10/1974 | Oliverius | 141/390 X |
| 4,485,855 | 12/1984 | Dillingham | 141/390 X |
| 4,520,926 | 6/1985 | Nelson | 206/366 |
| 4,569,344 | 2/1986 | Palmer | 604/171 X |
| 4,600,112 | 7/1986 | Shillington et al. | 206/366 X |
| 4,772,275 | 9/1988 | Erlich | 206/364 X |

*Primary Examiner*—Dalton L. Truluck
*Attorney, Agent, or Firm*—Alexander F. Norcross

[57] ABSTRACT

A device for removing monitoring tubes, especially nasogastric tubes, which have come in contact with bodily secretions from hospitalized patients, in a sanitary manner using a plastic housing canister open at both ends in which is affixed a long, thin plastic sheath. The device is used by removing the attached cap and introducing the free end of the monitoring tube into the mouth of the canister and then into the blind tip of the fully retracted sheath. One hand grasps the indwelling tube by grasping the surrounding sheath and the tube and gently pulling the sheath and tube to its fullest extension. The completely encased tube remains in the sheath and the cap is replaced over the canister for disposal in a sanitary fashion.

2 Claims, 1 Drawing Sheet

SECRETION CONTAMINATED INDWELLING TUBE CLOSED REMOVAL AND DISPOSAL SYSTEM

BACKGROUND OF THE INVENTION

This invention relates to the need to provide sanitary removal and disposal of patient monitoring tubes, especially nasogastric tubes from hospitalized or other patients. Special emphasis is placed on avoiding nurse or physician contact with bodily secretions of infectious patients.

The invention may best be described by reference to the ordinary procedure involved in the use of monitoring tubes, especially nasogastric tubes. Such tubes are routinely used for a variety of patients, usually those hospitalized for surgery or treatment for various diseases. A nasogastric tube is inserted through the nose into the stomach and is in contact with oral and gastrointestinal secretions. A major problem in the use of such tubes is sanitary removal and disposal. This is especially true for infectious patients, particularly those suffering from Acquired Immune Deficiency Syndrome (AIDS). Because bodily secretions can spread many diseases and because monitoring tubes invariably come in contact with such secretions, it is of paramount importance that the tube be removed and disposed without risk of contact by another person.

Currently, removal and disposal have been unsatisfactory with respect to sanitation in that the tubes are withdrawn from the patient in an open fashion; (i.e. not into a container). Although most hospital personnel will use gloves to do this, the end of the tube is difficult to control and often will swing uncontrollably once the tip is free of the patient's body. This may lead to spraying of bodily secretions or dripping of bodily secretions from the end of the tube. Also, the tube may swing and strike the remover or anyone else in the room. Currently, the tube is placed in an open waste receptacle which is lined with a plastic bag. It will sit in the receptacle until the bag is sealed (usually the end of the hospital shift which could be 8 - 12 hours). The open tube is also available to be contacted by individuals disposing of the plastic bag since it sits open and exposed in the bag.

Attempts at placing a towel or clean cloth or paper pad on the patient or bed to receive the tube is futile as the tube is still not removed under a controlled situation.

Consequently, there is no readily available closed system for disposal of these contaminated tubes at this time. The advantages to closed system removal and disposal should be obvious.

SUMMARY OF INVENTION

The invention discloses a form of plastic disposable canister, titled by the inventors the Secretion Contaminated Indwelling Tube Closed Removal and Disposal System, which has been developed and is suitable for removing and disposing of patient monitoring tubes in a sanitary fashion. The principle development of the canister has been for the removal and disposal of nasogastric tubes, but is also useful for use with any monitoring tube or any contaminated tube or long soft object (bladder catheter, rectal tube or endotracheal tube) that requires sanitary disposal.

Currently, there is no known device for a one-step removal/disposal technique such as performed by the invention.

The inventive canister consists of a small plastic canister, similar to a 35 mm. photography film canister to which is attached by a plastic tether a plastic canister cap. The canister is open at both ends. An inner canister is melded at the beveled mouth of the housing canister. A long, thin plastic sheath, blind at one end and opened at the other is collapsed into the inner canister. The entire device is made of plastic.

The device is used by inserting the free end of a monitoring tube into the blind pouch and opening of the canister. The device is activated by pulling the retracted sheath out of the canister along with the tube being removed. Upon completion, the fully extended sheath will contain the entire monitoring tube, which has been pulled passed the beveled mouth of the canister into the fully extended sheath. Thereafter, the tethered cap may be replaced upon the beveled mouth making a sealed package within which the tube is separated from contact with other persons or surfaces. The entire package is then disposed of.

It is thus an object of this invention to provide a device for sanitary removal of monitoring tubes from patients without allowing contact between the used tube and any other person or surface.

It is further an object of this invention to provide a convenient and compact, sealed unit for disposal of a used monitoring tube.

These and other advantages of the invention will be apparent to those skilled in the art from the detailed description of the preferred embodiment which follows.

DETAILED DESCRIPTION OF THE PREFERRED EMBODIMENT

Figure 3:
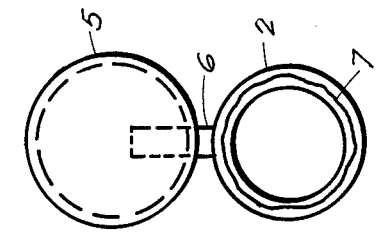
FIG. 3 is an illustrative depiction of the canister with the plastic sheath extended and occupied by a monitoring (nasogastric) tube which has been withdrawn from a patient.
Figure 2:
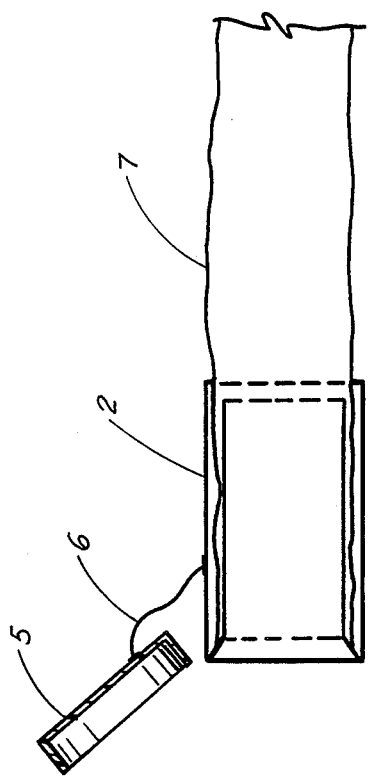
FIG. 2 is an end view showing the inner canister, housing canister and the packed plastic sheath between them.
Figure 1:
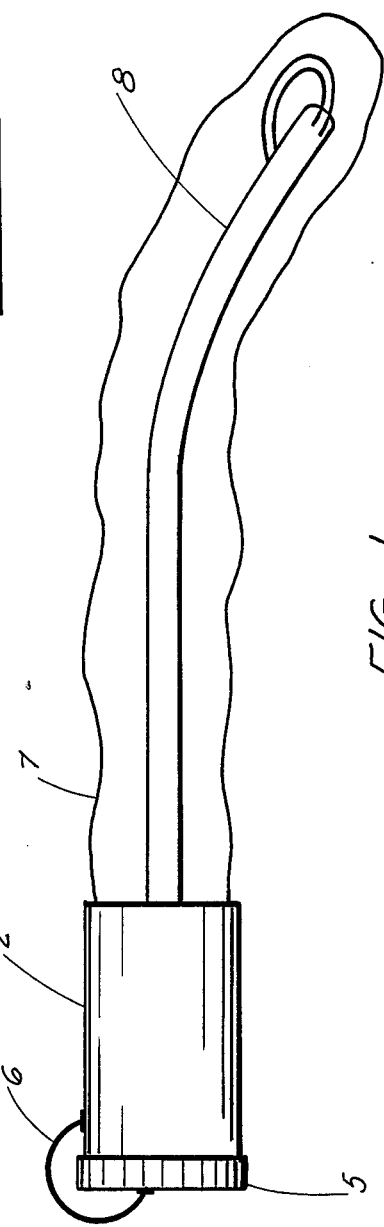
FIG. 1 is a side view showing the cap, canister, housing and plastic sheath of the current invention.

This device is designed to remove monitoring tubes, especially nasogastric tubes, from hospitalized patients in a sanitary manner with special emphasis on avoiding nurse or physician contact with the body secretions of infectious patients. This device consists of a housing canister (1) open at both ends. An inner canister (2) is melded at the beveled mouth (4). A long, thin plastic sheath (3) is first packed in the space between canister (1) and (2). The sheath (3) is a blind pouch at one end and melded to the beveled mouth (4) at the other end. A cap (5) securely fits over the beveled mouth (4). It is attached to the outer canister (1).

The device is used in the following manner. The cap (5) is opened. The monitoring tube (8) to be removed (any indwelling tube) is introduced by its free end to the beveled mouth (4) and passes into the blind tip of the fully retracted sheath (3). One hand grasps the indwelling tube through the sheath while the other holds the canister near the patient's body and with a gentle, even pull, the contaminated tube (8) is removed from the patient. Now the sheath (7) extends from the canister a length adequate to completely encase the removed indwelling tube. The cap (5) is then replaced. The entire unit is disposed with minimal risk of contamination of hospital personnel.

In order to illustrate the operative aspect and function of the current invention, the preferred description has concentrated on the field of removal of nasogastric tubes, which represents the preferred environment known to the inventor at this time. However, it is obvious that this invention has equal utility in any environment which is necessary to remove and dispose of a contaminated tube in a closed system. Therefore, although such procedures are not here disclosed, their use should be obvious to those of ordinary skill in the art; it is suggested that this disposal system would be of equal utility for such procedures as removal of indwelling vascular catheters or any other indwelling bodily catheter or monitoring tube.

Therefore, the invention is not limited to the specific operative embodiments disclosed above but rather to that wider class of disposal systems as claimed.

I claim:

1. An apparatus for isolated, sanitary reception and disposal of a contaminated tube comprising:

a rigid, tubular, hand-held canister having a first and a second open end therein;

means for sealingly capping said first end;

an elongate, impervious flexible sheath having an open receiving end;

said sheath being sealingly affixed at said open end interior to said receptacle means, having a first collapsed position within said receptacle and a second, extended enclosing position distal of the second end of said receptacle;

the first open end of said hand-held canister having means for directing the free end of a contaminated tube to the interior of said canister within said sheath;

said means for directing said free end comprising an inwardly extending bevel extending circumferentially around said open mouth.

2. A process for removing and disposing of contaminated tubes comprising:

providing a tubular hand-held member having an extensible shielding flexible sheath affixed therein;

said hand-held member defining an enclosed opening therein;

manipulating said hand-held member over a free end of a contaminated tube without external contact thereto;

extending said hand-held member distal of the free end of said contaminated tube, protruding said free end through a second end of said hand held member, said free end being enclosed within a closed end of said sheath;

grasping said sheath, trapping the free end of said contaminated tube therein;

pulling said contaminated tube through said hand held member until such tube is fully enclosed within said sheath; and occlusally sealing the opening of said hand held member.

* * * * *